(12) United States Patent
Gupta

(10) Patent No.: US 6,689,275 B1
(45) Date of Patent: *Feb. 10, 2004

(54) METHOD AND PHARMACEUTICAL COMPOSITION FOR REPLACING IRON LOSSES IN DIALYSIS PATIENTS

(76) Inventor: Ajay Gupta, 39151 Horton, Farmington Hills, MI (US) 48331

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/775,595

(22) Filed: Dec. 31, 1996

(51) Int. Cl.⁷ .............................................. A01K 33/26

(52) U.S. Cl. ...................... 210/647; 210/646; 424/603; 424/646; 424/647; 604/7; 604/27; 604/29

(58) Field of Search ............................. 604/29, 27, 7; 530/417; 424/603, 646, 647, 910; 210/646, 647

(56) References Cited

U.S. PATENT DOCUMENTS

| | | | |
|---|---|---|---|
| 3,911,915 A | * 10/1974 | Seifter et al. ................ | 424/180 |
| 4,315,942 A | 2/1982 | Corden ........................ | 424/295 |
| 4,756,838 A | 7/1988 | Veltman ........................ | 252/1 |
| 4,867,963 A | * 9/1989 | Maurer et al. .................. | 424/9 |
| 5,108,767 A | 4/1992 | Mulchandani et al. ......... | 426/72 |
| 5,393,777 A | 2/1995 | Crosa .......................... | 514/502 |
| 5,906,978 A | 5/1999 | Ash ............................. | 514/23 |

OTHER PUBLICATIONS

The Merck Index, Merck and Co, Inc, Rahway, NJ, Budavari Ed, 11th Edition, page 3969, 1989*
Dorland's Illustrated Medical Dictionary, WB Saunders Co 27th Edition pages 462, 741, 837, 1541, 1985*
Berner et al J Nutr Vol 115 1042–1049, 1985*
Hazell et al Br J Nutr Vol 39 631–639, 1978*
Sunder–Plassmann et al Nephrol Dial TRansplant Vol 11 1797–1802, 1996*
Rubinger et al Amer J Kidney Diseases VOL VII No 2 125–129, Feb. 1986*
Zanen et al Nephrol Dial Transplat Vol 11 820–824, 1996*
Erslev (1991) Drug Therapy. *N. Engl. J. Med.*, 329(19):1339–1344.
Moore et al., (1992) Incidence, causes, and treatment of iron deficiency anemia in hemodialysis patients. *J. Renal. Nutrition*, 2:105–112.
Kleiner et al. (1995) The role of iron and other factors in patients unresponsive to erythropoietin therapy. *Seminars in Dialysis*, 8:(1):29–34.
Konopka et al. (1981) Iron transfer from transferrin to ferritin mediated by polyphosphate compounds. *Biochem. Biophys. Acta.*, 677:417–423.
Konopka et al. (1980) Iron transfer from transferrin to ferritin mediated by pyrophosphate. *Biochem. Biophys. Acta.*, 96(3):1408–1413.
Morgan (1977) Iron exchange between transferrin molecules mediated by phosphate compounds and other cell metabolites. *Biochim. Biophys. Acta.*, 499(1):169–177.
Kolff (1965) First clinical experience with artificial kidney. *Ann. Intern. Med.*, 62:608.
Scribner et al. (1960) The treatment of chronic uremia by means of intermittent hemodialysis; a preliminary report. *Trans. Amer. Soc. Artif. Int. Organs*. 6:114.
Jacobs et al., (1985) Isolation and characterization of genomic and cDNA clones of human erythropoietin. *Nature*, 313:806–810.
Levin (1992) The impact of epoetin alfa: quality of life and hematocrit level. *AM. J. Kid. Dis.*, XX (Suppl 1 (Jul.)):16–20.
Eschbach et al. (1977) Iron balance in hemodialysis patients. *Ann. Intern. Med.*, 87:710–713.
Macdougall et al., (1992) Detection of functional iron deficiency during erythropoietin treatment: a new approach. *Br. Med. J.* 304:225–226
Van wyck et al., (1989) Iron status in patients receiving erythropoietin for dialysis–associated anemia. *Kidney Int.*, 35:712–716.
Wingard et al., (1995) Efficacy of oral iron therapy in patients receiving recombinant human erythropoietin. Am. J. Kid. Dis., 25:433–439.
Macdougall et al., (1989) Poor response to the treatment of renal anaemia with erythropoietin corrected by iron. . . *Br. Med. J.*, 299:157–158.
Schaeffer and Schaefer (1995) The hypochromic red cell: a new parameter for monitoring or iron supplementation. . .*J. Perinat. Med.*, 23:83–88.
Horl (1996) How to diagnose and correct iron deficiency during r–huEPO therapy — a consensus report. *Nephrol. Dial. Transplant.* 11:246–250.
Sepandj et al., (1996) Economic appraisal of maintenance parenteral iron administration in treatment of anaemia in chronic. . . *Nephrol. Dial. Transplant.*, 11:319–322.
Rosenlof et al., (1995) Iron availability is transiently improved by intravenous iron medication in patients. . . *Clin. Nephrol.*, 43:249–255.
Fishbane and Lynn (1995) The utility of zinc protoporphyrin for predicting the need for intravenous iron therapy. . . *Am. J. Kidney Dis.*, 25:426–432.

(List continued on next page.)

Primary Examiner—Susan Ungar
Assistant Examiner—Minh-Tam Davis
(74) Attorney, Agent, or Firm—Drinker Biddle & Reath LLP

(57) ABSTRACT

A method of replacing iron losses during dialysis of patients is accomplished by infusion of a noncolloidal ferric compound, soluble in hemodialysis solutions, during dialysis. A pharmaceutical composition is provided consisting essentially of dialysis solution including a soluble noncolloidial ferric compound, preferably ferric pyrophosphate.

4 Claims, 1 Drawing Sheet

OTHER PUBLICATIONS

Macdougall et al. (1993) A randomized controlled study of iron supplementation in patients treated with erythropoietin. *J. Am. Sec. Nephrol.*, 4:428 (abstract).

Sunder–Plassmann and Horl. (1995) Importance of iron supply for erythropoietin therapy. *Nephrol. Dial. Transplant.* 10:2070–2076.

Schaeffer and Schaefer (1992) Management of iron substitution therapy during r–HuEPO therapy in chronic renal failure patients. *Erythropoiesis*, 3:71–75.

Nyvad et al. (1994) Intravenous iron–sucrose complex to reduce epoetin demand in dialysis patients. *Lancet*, 344:1305–1306.

Hamstra et al. (1980) Intravenous iron dextran in clinical medicine. *JAMA*, 243:1726–1731

Kumpf and Holland (1990) Parenteral iron dextran therapy. *DICP Ann Pharmacother*, 24:162–166.

Weinberg (1984) Iron withholding: a defense against infection and neoplasia. *Physiol. Rev.*, 64–65–102.

Heath et al., (1932) Quantitative aspects of iron deficiency in hypochromic anemia. *J. Clin. Invest.*, 11:1293.

Best and Taylor, (1943) in *The Physiological Basis of Medical Practice*, The Williams 6 Wilkins Co., Baltimore, MD pp.94–99.

Brown et al. (1950) Intravenously administered saccharated iron oxide in the treatment of hypochromic anemia. *JAMA*, 144:1084–1089.

Nissim, (1947) Intravenous administration of iron. *Lancet*, 2:49–51.

Cox et al., (1965) Valency investigations of iron dextran ('Imferon'). *Nature*, 207:1202–1203.

Hatton et al., (1995) Removal of iron dextran by hemodialysis: as in vitro study. *Am J. Kid. Dis.*, 26(2):327–330.

Pascual et al. (1992) Intravenous Fe–Gluconate–Na for iron–deficient patients on hemodialysis. *Nephron*, 60:121.

Allegra et al., (1991) Iron deficiency in maintenance hemodialysis patients: assessment of diagnosis criteria. . . *Nephron*, 57:175–182.

Pollack and Weaver, (1965) Guinea pig and human red cell hemolysates release iron from transferrin. *J. Lab. Clin. Med.*, 105(5):629–634.

Pollack et al., (1977) Iron removal from transferrin. An experimental study. *Biochim. Biophys. Acta.*, 497(2):481–487.

Morgan (1979) Studies on the mechanism of iron release from transferrin. *Biochim. Biophys. Acta*, 580(2):312–326.

Carver and Frieden (1978) Factors affecting the adenosine triphosphate induced release of iron from transferrin. *Biochemistry*, 17(1):167–172.

Nilsen and Romslo (1984) Pyrophosphate as a ligand for delivery of iron to isolated rat–liver mitochondria. *Biochim. Biophys. Acta.*, 766(1):233–239.

Javiad et al., (1991) Interactions between infections, malnutrition and iron nutritional status in Pakistani infants. . . *Acta Paediatrica Scandinavica —Supplement*, 374:141–50.

Bryd and Horwitz, (1991) Lactoferrin inhibits or promotes Legionella. pneumophila intracellular multiplication. . . . *J. Clin. Invest.*, 88(4):1103–1112.

Ristroph et al., (1981) Chemically defined medium for Legionella pneumphila growth. *J. Clin. Microbiology*, 13(1):115–119.

Feeley et al., (1978) Primary isolation media for Legionnaires disease bacterium. *Journal of Clinical Microbiology*, 8(3):320–5.

Maurer et al., (1990) Paramagnetic pyrophosphate. Preliminary studies on magnetic resonance contrast enhancement of acute myocardial. . . *Investigative Radiology*, 25(2):153–63.

Stevenson et al. (1974) The toxicity of Sn–pyrophosphate: clinical manifestations prior to acute LD50. *J. Nucl. Med.*, 15:252–256.

Harken et al., (1981) Early ischemia after complete coronary ligation in the rabbit, dog, pig and monkey. *Am. J. Physiol.*, 241:H202.

Sillen and Martell (1964) Stability constants of metal–ion complexes. *The Chemical Society*, London, (select pages only).

Kornberg (1962) On the metabolic significance of phosphoroltyic and pyrophosphorolytic reactions. In Kasha M, Pullman B, eds. *Horizons on Biochemistry*, New York, Academic Press, pp.251–264.

Jung et al., (1970) The fate of intravenously injected 32–p–pyrophosphate in dogs. *Amer. J. Physiol.*, 218:1757.

Fleisch and Bisaz (1962) Mechanism of calcification: inhibitory role of pyrophosphate. *Nature (Lond.)*, 195:911.

Fleisch (1995) in Fleisch H, ed., *Bisphosphanates in bone disease: from the laboratory to the patient*. 2nd ed. Carnforth, Lancs, England: the Parthenon Publishing Group Ltd., pp. 31–33.

Ifudo et al., (1996) The intensity of hemodialysis and the response to erythropoietin in patients with end stage renal disease. *N. Engl. J. Med.*, 334:420–425.

Cheuk et al., (1987) Kinetics of pyrophosphate induced iron release from diferric ovotransferrin. *J. of Inorganic Biochemistry*, 29:301–311.

Fishbane et al., (1995) Reduction in recombinant human erythropoietin doses by the use of chronic intravenous iron supplementation *Am. J. Kidney Diseases*, 26:41–46.

Hurrett et a1., (1989) Iron fortification of infant cereals: a proposal for the use of ferrous fumarate. . . *Am. J. Clin. Nutr.*, 49:1274–62.

Schibler (1968) Inhibition by pyrophosphate and poly–phosphate of aortic calcification induced by vitamin D, in rats. *J. Clin. Sci.*, 35:363–372.

Starkenstein E., "Beiträge zur Pharmakologie des Eisens." *Archiv für experiment, Path. u. Pharmakol.* 118:131–191 (1921).

Yoshifumi Tsuji et al., *Eur. J. Surg.*, "Effect of Recombinant Human Erythropoietin on Anaemia after Gastrectomy: A Pilot Study", 161: 29–33 (1995).

Shimamatsu, *nephrol Dial Transplant*, "Experience with i.v. iron chonodrointin–sulphate colloid in Japanese haemodialysis patients", 13: 1053 (1998).

*The National Formulary* VII, p. 165 (1942).

Dainippon Pharmaceutical product description for BLUTAL® Injection, p. 175–177 (1994).

Provisional patent application Ser. No. 60/023,926, filed Aug. 14, 1996.

Basta, S.S., et al. Iron deficiency anemia and the productivity of adult males in Indonesia. *Am.J.Cllin.Nutr.* 1979; 32:916.

Brown, E.B., et al. Intravenously administered saccharated iron oxide in the treatment of hypochromic anemia. *JAMA*, 1950; 144:1084–1089.

Calvar, C., et al., Intravenous administration of iron gluconate during hemodialysis. *Nephrol. Dial. Transplant.* 1997; 12:574–575.

Cook, J.D., et al., Iron deficiency: The global perspective. In.: Hershko, C. ed. *Progress in Iron Research*, New York: Plenum Press, 1994:219–228.

Fishbane, S., et al., The safety of intravenous iron dextran in Hemodialysis Patients. *Am. J. Kidney Dis.* 1996; 28:529–534.

Lieberman, E., et al., Association of maternal hematocrit with premature labor. *Am. J. Obstet. Gynecol.* 1988; 159:107.

Lozoff, b., et al., Long–term developmental outcome of infants with iron deficiency. *N Engl J Med*, 1991; 325:687.

NKF–Doqi clinical practical guidelines for the treatment of anemia of chronic renal failure. *Am.J.Kid.Dis.*, 1997; 30:S192–S137.

Ohira, Y., et al., Work capacity, heart rate and blood lactate responses to iron treatment. *Br.J. Haematol.* 1979; 41:365.

Oski, F.A., et al., The effects of therapy on the developmental scores of iron–deficient infants. *Pediatrics* 1978; 92:21.

Oski, F.A., et al., Effect of iron therapy on behavior performance in nonanemic, iron–deficient infants. *Pediatrics* 1983; 71:877.

Schultink, W., et al., Low compliance with an iron–supplementation program: a study among pregnant women in Jakarta, Indonesia. *Am. J. Clin. Nutr.* 1979; 32:916.

Stockman, R. The treatment of chlorosis by iron and some other drugs. *Br. Med. J.*, 1893; I:881–885.

\* cited by examiner

METHOD AND PHARMACEUTICAL COMPOSITION FOR REPLACING IRON LOSSES IN DIALYSIS PATIENTS

TECHNICAL FIELD

The present invention relates to hemodialysis and more particularly to methods of supplementing dialysate solutions for the treatment of iron deficiency in diaylsls patients.

BACKGROUND OF THE INVENTION

Patients with chronic renal failure suffer from anemia due to impaired production of erythropoietin [Erslev, 1991]. Clinical manifestations of chronic renal failure improve as uremia and volume overload were corrected by dialysis. However, anemia due to lack of erythropoieatin becomes a major limiting factor in the functional well being of end stage renal disease patients.

Molecular cloning of the erythropoietin gene in 1985 [Jacobs et al., 1985] led to commercial production of recombinant erythropoietin, which was a major advance in the treatment of renal anemia [Erslev, 1991; Levin, 1992]. Erythropoietin therapy functions by stimulating red cell production and thereby iron utilization. With the use of erythropoietin therapy, transfusions are avoided in most chronic dialysis patients. However, accelerated iron utilization coupled with small but unavoidable loss of extra corporeal blood with hemodialysis and increased gastrointestinal losses of iron lead to iron deficiency in almost all patients on long term maintenance dialysis.

Other factors that may contribute to an iron deficient state are restricted renal diet which may be deficient in iron, and iron absorption may be impaired by uremia per se. Administration of additional medication such as phosphate binders with food may also impair iron absorption. Therefore, iron deficiency has become a major problem in the maintenance of hemodialysis patients treated with erythropoietin.

Van Wyck et al., 1989, have suggested that all renal patients with low to normal iron stores should prophylactically receive iron. Iron supplementation is accomplished most conveniently by the oral administration of iron one to three times a day.

A problem exists because oral iron is often not tolerated due to gastrointestinal side effects. Practical problems such as noncompliance, impaired absorption when taken with meals, and other factors are further combined with the problem of tolerating oral iron. It is also ineffective due to impaired iron absorption. Macdougall et al., 1989, also found a retarded response to recombinant human erythropoietin in hemodialysis patients on oral iron, which was corrected once, iron was given intravenously. Schaefer and Schaefer, 1995, have recently demonstrated that only intravenous but not oral iron guarantees adequate marrow iron supply during the correction phase of recombinant erythropoietin therapy.

In Europe, iron is available for intravenous administration as iron dextran, iron saccharate and iron gluconate. In the United States, only iron dextran is approved for intravenous use and is widely used for this purpose in dialysis patients. However, there are controversies with regard to the dosage and frequency of injection.

On the one hand, intravenous iron therapy has several advantages over oral administration. Intravenous therapy overcomes both compliance problems and the low-gastrointestinal tolerance often observed in patients on oral therapy. Schaefer and Schaefer, 1992, reported a 47% reduction in erythropoietin dose, when intravenous iron was given to iron deficient hemodialysis patients previously treated with oral iron. On the other hand, intravenous iron therapy does have risks and disadvantages. Anaphylactoid reactions have been reported in patients [Hamstra et al., 1980; Kumpf et al., 1990]. Therefor, a test dose must be administered when parenteral iron therapy is first prescribed. Intravenous iron therapy can also cause hypotension, loin and epigastric pain during dialysis which may be severe enough to stop the treatment. Further, the intravenous drug is expensive and requires pharmacy and nursing time for administration.

In view of the above, neither the oral nor intravenous iron therapy route is ideal and alternative routes of iron administration are desirable for dialysis patients.

Infusion of iron during dialysis appears similar to an intravenous infusion, albeit at a slower rate. However, iron is known to be toxic when administered parenterally in its mineral form. The toxic effects may arise from precipitation of iron in the blood, producing multiple pulmonary and sometimes systemic emboli. Symptoms resembling that of fat embolism occur. Irritation of the gastrointestinal tract gives rise to diarrhea and vomiting. Also, depression of the central nervous system can lead to coma and death [Health et al., 1982].

Very few noncolloidal iron compounds are suitable for intravenous administration. In the last five years, at least two groups of researchers have, administrated ferric gluconate sodium intravenously for the treatment of iron deficiency in chronic hemodialysis patients [Pascual et al., 1992; Allegra et al., 1981]. In these and various other studies, solubility, bioavailability and toxicity of various ferric compounds were shown to be different.

Recent studies have shown that polyphpsphate compounds are possible candidates for intracellular iron transport [Konopka et al., 1981; Pollack et al., 1985]. Among these polyphosphate compounds, pyrophosphate has been shown to be the most effective agent in triggering iron removal from transferrins [Pollack et al., 1977; Morgan, 1979; Carver et al., 1978]. Pyrophosphate has also been shown to enhance iron transfer from transferrin to ferritin [Konopka et al., 1980]. It also promotes iron exchange between transferrin molecules [Morgan, 1977]. It further facilitates delivery of iron to isolated rat liver mitochondria [Nilson, et al., 1984].

The U.S. Pat. No. 4,756,838 to Veltman, issued Jul. 12, 1988, discloses a dry, free flowing, stable readily soluble, noncaking, particulate soluble products which are readily soluble in water and are useful for preparing solutions for use in hemodialysis. The patent discloses the fact that currently used dialysis procedures do not ordinarily take into account those materials in blood that are protein bound. Examples are iron, zinc, copper, and cobalt. The patent states that it is an object of the invention to make such materials as an integral part of dry dialysate products. However, no specific disclosure is made on how to make the iron available through the hemodialysis. No direction is given towards a noncolloidal iron compound as opposed to any other iron compound or mineral iron.

Ferric pyrophosphate has been used for iron fortification of food and for oral treatment of iron deficiency anemia [Javaid et al., 1991]. Ferric pyrophosphate has also been used for supplying iron to eukaryotic and bacterial cells, grown in culture [Byrd et al., 1991]. Toxic effects of ferric pyrophosphate have been studied by Mauer and coworkers in an animal model [Maurer et al., 1990]. This study showed an $LD_{50}$ slightly higher than 325 mg of ferric pyrophosphate per kilogram or approximately 35 milligrams of iron per kilogram body weight. The effective dose for replacing iron losses in hemodialysis patients is estimated to be 0.2 to 0.3 milligrams iron per kilogram per dialysis session. Therefore, the safety factor (ratio of $LD_{50}$ to effective dose) is over 100.

Studies with another metal pyrophosphate complex, stannous pyrophosphate have reported immediate toxic effects. Since ferric ion forms a stronger complex to pyrophosphate than do stannous ion or calcium ion, [Harken et al., 1981; Sillen et al., 1964], hypocalcemia is not a known side affect of ferric pyrophosphate administration.

In view of the above, it is desirable to administer iron to a large proportion of dialysis patients by adding a soluble, non-colloidal iron compound to dialysis solutions, in order to replace ongoing losses of iron or to treat iron deficiency.

SUMMARY OF THE INVENTION

In accordance with the present invention, there is provided a method of administering iron in dialysis patients by infusion of a noncolloidal ferric compound, soluble in dialysis solutions during dialysis. The present invention further provides a pharmaceutical composition consisting essentially of a hemodialysis solution including a soluble, noncolloidal ferric compound. Preferably, the ferric compound is ferric pyrophosphate.

BRIEF DESCRIPTION OF THE FIGURES

Other advantages of the present invention will be readily appreciated as the same becomes better understood by reference to the following detailed description when considered in connection with the accompanying drawings wherein.

DETAILED DESCRIPTION OF THE INVENTION

Figure 1A:
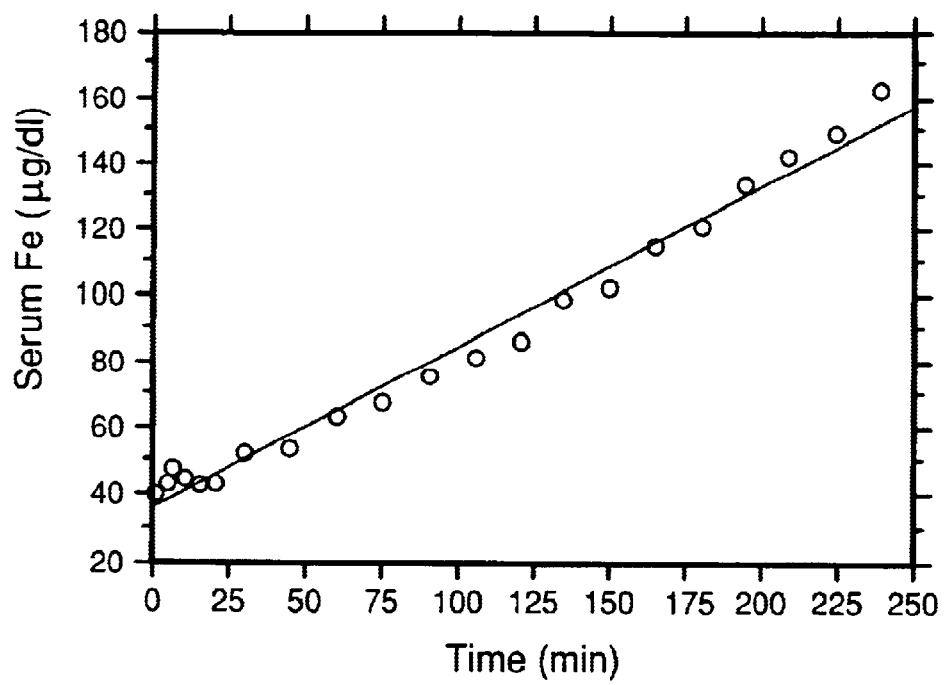
FIG. 1A is a graph showing serum iron versus time and 1B is a graph showing iron per TIBC (percent) versus time.

In accordance with the present invention, there is provided a method of administration of iron in dialysis patients by infusion of a noncolloidal ferric compound, soluble in hemodialysis solutions, during dialysis. Administration can be to patients on hemodialysis (acute or maintenance) or peritoneal dialysis.

More specifically, as discussed above, hemodialysis patients are those patients undergoing hemodialysis for renal failure. Long-term hemodialysis therapy for treatment of end stage renal failure is referred to as maintenance hemodialysis. Patients on maintenance hemodialysis have been estimated to lose about 2 to 3 grams of iron per year, corresponding to approximately 6 ml per day (2 liters per year) blood loss from all sources [Eschbach et al., 1977]. These patients receive hemodialysis three times per week.

A specific example of a hemodialysis system is the Fresenius system. In the Fresenius system, the ratio of acid:bicarbonate:water:total is 1:1.23:32.77:35. Therefore, one part of the concentrated bicarbonate solution is mixed with 27.5 parts of the other (acid+water), to make the final dialysate. In order to make the bicarbonate concentrate, purified water is pumped from the purified water source by a pipe into a large tank Fresenius supplies sodium bicarbonate powder packaged in plastic bags and the contents of each bag are mixed with purified water in the tank, to make 25 gallons (94.6 liters) of bicarbonate solution. After thorough mixing with a stirrer the concentrated solution is run into 20 liter plastic receptacles that are capped. The concentrate is prepared within 24 hours of its use. Ferric pyrophosphate is freely soluble in the bicarbonate concentrate. Ferric pyrophosphate is pre-weighed and supplied packaged in plastic vials to the dialysis units. For a dialysate iron concentration of 4 $\mu$g/dl or FePyP concentration of 40 $\mu$g/dl, it can be calculated that bicarbonate concentrate should have a ferric pyrophosphate concentration of 40×27.5=1100 $\mu$g/dl, or 11 mg/liter. Therefore, 1040 mg of ferric pyrophosphate added to 94.6 liter (25 gallons of bicarbonate concentrate will generate dialysate with an iron concentration of 4 $\mu$g/dl.

TABLE 1

Bicarbonate concentrates with a defined iron concentration achieved by addition of FePyP.

| Required Conc. of Fe in dialysate | Estimated Conc. of FePyP in dialysate | Estimated Amount of FePyP in concentrate |
| --- | --- | --- |
| 2 $\mu$g/dl | 20 $\mu$g/dl | 5.5 mg/L |
| 4 $\mu$g/dl | 40 $\mu$g/dl | 11 mg/L |
| 8 $\mu$g/dl | 80 $\mu$g/dl | 22 mg/L |
| 12 $\mu$g/dl | 120 $\mu$g/dl | 33 mg/L |

Dialysate Fe concentration can be increased adding different amounts of FePyP to the bicarbonate concentrate (Table 1). The technician preparing the concentrate would be required to add dry bicarbonate powder and ferric pyrophosphate crystals at the same time to purified water and the solution would be gently stirred until both compounds have dissolved resulting in a clear solution. Plastic receptacles are filled with bicarbonate concentrate containing iron and marked with the specific concentration of iron. This is to ensure that patients receive the prescribed concentration of dialysate iron therapy.

Figure 1B:
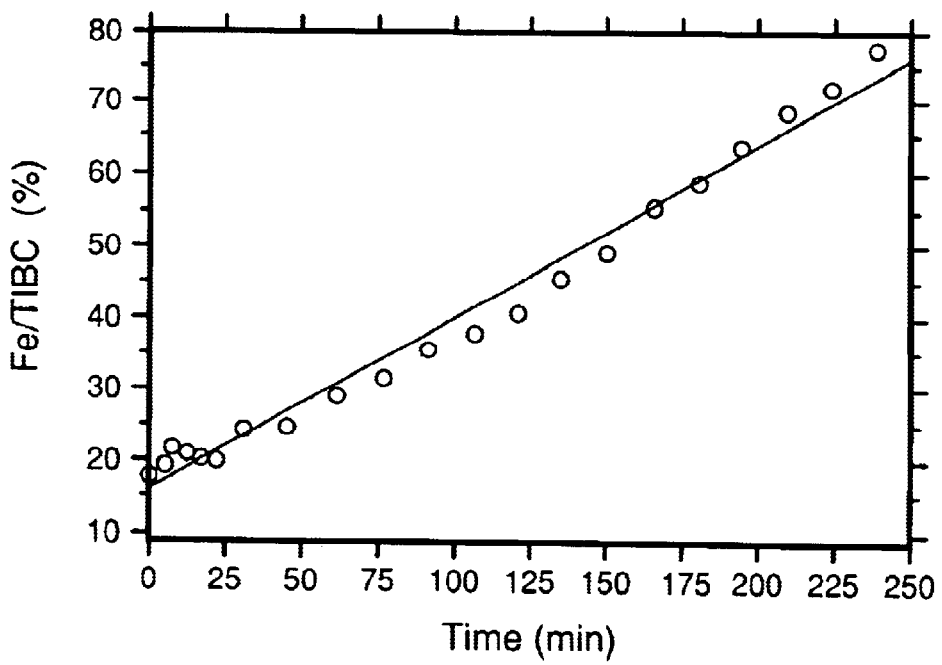

In a previous experiment, plasma (3.5 liters) was dialyzed using an F-80 dialyzer with the plasma flow rate set at 300 ml/min. and the dialysate flow rate 800 ml/min. Ferric pyrophosphate (420 mg) was added to 20 liters of bicarbonate concentrate and intermittently stirred for one hour prior to the dialysis. This was a clear solution with a light greenish yellow tinge. The final dialysate was a clear, colorless solution, with 5 $\mu$g/dl iron content, as measured by a calorimetric assay. Physiological saline solution was added to the plasma every 15 minutes to compensate for obligate ultrafiltration, and to keep the plasma volume constant. Serum Fe and TIBC were measured at frequent intervals. There was a progressive increase in plasma iron concentration as shown in FIG. 1A, and transferrin saturation as shown in FIG. 1B.

By hemodialysis, it is meant that a hemodialyzer is used to remove certain solutes from blood by virtue of their concentration gradients across a semipermeable membrane. Such membranes may be reused for a single patient. The hemodialyzer is an apparatus by which hemodialysis is performed, blood being separated by the semipermeable membrane from a solution of such composition as to secure diffusion of certain solutes from the blood. The hemodialyzer is popularly called an artificial kidney. The hemodialyzer can be used for ultrafiltration by which differences in fluid pressure bring about filtration of a protein-free fluid from the blood.

The hemodialysis solution of the present invention is characterized by including a noncolloidal ferric compound, preferably having a molecular weight of less than 1000 daltons. Most preferably the ferric compound should be 1) soluble in hemodialysis solutions in adequate concentrations; 2) efficiently transfer from the dialysate to the blood compartment; 3) bind to transferrin in the-plasma and be available for use by tissue; 4) be well tolerated without any short or long term side effects; and 5) be economical. In view of these parameters, ferric pyrophosphate is the preferred compound for use with the present invention.

Ferric pyrophosphate ($Fe_4O_{21}P_6$) has a molecular weight of 745.25. It has been used as a catalyst, in fireproofing synthetic fibers and in corrosion preventing pigments.

In use, hemodialysis machines utilize an automated proportioning system to mix a sodium bicarbonate concentrate, an acid concentrate containing sodium chloride, potassium chloride, calcium chloride, sodium acetate, and glucose, and deionized water in specific proportions to generate the final dialysate solution. The dialysate concentrates are usually supplied by the manufactures either as a solution ready to use or as a premixed powder that is added to purified water in large reservoirs.

After thorough mixing, the bicarbonate concentrated solutions are packaged into approximately 20 liter plastic jugs. The acid or bicarbonate concentrates may be prepared the same day or a day prior to their use. The two concentrates are pumped into a chamber in the dialysis machine where they are mixed with purified water to make the final dialysate solution.

Generally, the ionic composition of the final dialysate solution is as follows: $Na^+$ 137–143 mEq/L, $K^+$ 0–4.0 mEq/L, $Cl^-$ 100–111 mEq/L, $Mg^2$ 0.75–1.5 mEq/L, $HCO_3^-$ 30–35 mEq/L, and acetate 2–4.5 mEq/L. The dialysate is pumped into the dialyzer at a flow rate of 0.5 to 1 liter per minute. After a single pass through the dialyzer, the spent dialysate is pumped back into the dialysis machine from which it exits into the drain.

In accordance with the present invention, the ferric pyrophosphate is added to the final dialysate by its addition to one or both of the dialysate concentrates. Since the concentrates are diluted several fold in the machine by admixture with water, the compound has to be added at a proportionally higher concentration in the concentrate or concentrates.

Preferably, 2 to 50 μg of iron is infused per deciliters of the hemodialysis solution to a patient during a dialysis treatment. Accordingly, 4 to 50 milligrams of iron are infused into the patient during a two to five hour hemodialysis session to the patient.

In view of the above, the present invention provides pharmaceutical composition consisting essentially of the hemodialysis solution including a soluble noncolloidal ferric compound, preferably ferric pyrophosphate.

It must be recognized that various specific solutions are utilized to formulate hemodialysis solutions.

The following studies demonstrate the preparation and utility of the present invention.

EXPERIMENTS

The following experiments were performed to demonstrate the solubility of ferric pyrophosphate in a final dialysate solution and the dialysate concentrates.

Methods: Ferric pyrophosphate ($Fe_4(P_2O_7)_3$, M. W. 745.2, CAS 10058-44-3) (hereinafter FePyP) is a greenish yellow crystalline compound that is known to have a solubility of 50 mg per ml. in warm water (Catalog No. P 6526; Sigma Chemical Co., St. Louis, Mo.). Initially a small amount of FePyP crystals were added to the acid (pH, 2.49) and basic (pH, 7.81) concentrates and the dialysate (pH, 7.15). FePyP dissolved readily in the dialysate and the bicarbonate concentrate, forming a yellow-orange solution. However there was incomplete dissolution in the acid concentrate, and a precipitate was clearly visible. Since the concentrated bicarbonate

TABLE 2

Concentration of iron in bicarbonate concentrate after the addition of ferric pyrophosphate

| Amount of FePyP added | Expected iron conc. | Measured conc. of Fe |
|---|---|---|
| 2 mg/ml | 0.2 mg/ml or 20 mg/dl | 20.250 mg/dl |
| 5 mg/ml | 0.5 mg/ml or 50 mg/dl | 40.660 mg/dl |
| 10 mg/ml | 1.0 mg/ml or 100 mg/dl | 94.500 mg/dl |
| 20 mg/ml | 2.0 mg/ml or 200 mg/dl | 206.500 mg/dl |

*note ~ 10% of FePyP is Fe solution is diluted several fold in the formation of the final dialysate, the concentration of FePyP in the bicarbonate concentrate should be appropriately higher than the desired dialysate concentration. Therefore solubility of FePyP in the bicarbonate concentrate was tested by adding variable amounts of FePyP and measuring the iron content of the mixture by the standard calorimetric method. The results are shown in Table 2. The measured and expected concentrations of iron were similar, showing that FePyP is highly soluble at the concentrations tested. A cler solution was formed within one hour of adding FePyP to the bicarbonate concentrate or the dialysate. Therefore, in dialysis practice, dialysate with a specific concentration of FePyP can be generated using a bicarbonate concentrate containing a proportionately higher concentration of FePyP.

In a second set of experiments, an in vitro dialysis of plasma, utilizing a conventional hemodialysis set up was used to show that the addition of even small amounts of ferric pyrophosphate to a dialysate solution results in significant transport of iron into the blood compartment during dialysis. This occurs because the transferred iron avidly binds to transferrin in the plasma.

Methods: Plasma was obtained from a uremic patient undergoing plasma exchange therapy for Goodpastures syndrome. Citrated plasma was stored at –20° C. in plastic bags. In three separate experiments plasma was dialyzed against dialysates with different concentration of Fe, prepared by adding variable amounts of FePyP to the bicarbonate concentrate. Dialyzers with a polysulfone membrane (Fresenius, USA) were used. When the volume of plasma being dialyzed was less than 1000 ml, a small dialyzer (F-4, Fresenius) with small blood volume (65 ml) and surface area (0.8 sq. meter) was used at a plasma flow rate of 100 ml/min. With a larger volume of plasma, a F-80 dialyzer with a priming volume of 120 ml and a surface area of 1.8 sq. meter was used at a plasma flow rate of 300 ml/min. Heparin (500 units per hour) was infused to prevent clotting in the circuit. Serum was drawn at regular intervals during the experiment and serum iron (Fe), total iron binding capacity (TIBC) and transferrin saturation (Fe/TIBC×100) were measured by a calorimetric assay. The obligate ultrafiltration of fluid during hemodialysis was compensated by a continuous infusion of 0.9% saline. The iron parameters were corrected for net ultrafiltration by expressing the results as transferrin saturation.

Results: There was an increase in serum iron and transferrin saturation with time when iron was added to the dialysate. The increment in serum Fe and transferrin saturation was more as the concentration of iron in the dialysate was increased. There was a near doubling of transferrin saturation after two hours of dialysis with a dialysate iron concentration of 8 μg/dl.

Experimental parameters were then chosen to mimic conditions that prevail in actual dialysis practice. Therefore, 3.5 liters of plasma (approximating the plasma volume in a 70 kg. patient) was dialyzed against a dialysate with 5 μg/dl Fe concentration. The results are shown in FIG. 1A and 1B.

The hourly increase in plasma iron concentration was 23, 23, 35 and 45 μg/dl, and the net increase in iron concentration was 140 μg/dl over the course of the experiment. FIG. 1A Therefore 5 mg iron (or ~50 mg FePyP) was infused into 3.5 liters of plasma, using a dialysate with 5 μg iron per dl. It should be noted that 420 mg of FePyP added to 20 liters of the bicarbonate concentrate imparted a very light greenish tinge to the solution, but after dilution with water the final dialysate was colorless.

In conclusion, ferric pyrophosphate can be added to the bicarbonate concentrate, aiming for an iron concentration of 2–50 μg/dl in the final dialysate depending on the degree of Fe deficiency. Hemodialysis with iron containing dialysate (Dialytic Iron Therapy) does result in transfer of iron to the blood compartment. In these in vitro experiments, maximum iron transfer cannot be obtained since transferrin is confined to a closed system. In vivo, the release of iron to the erythron and to the tissues by transferrin increases the total amount of iron that can enter the blood compartment. Therefore, dialysate iron therapy is a safe and effective route of iron delivery to hemodialysis patients.

In view of the above experiments, it is demonstrated that hemodialysis utilizing a hemodialysis solution containing iron compounds such as ferric pyrophosphate can be used to increase the amount of bioavailable iron in a mammal. The data demonstrates that the ferric pyrophosphate is soluble in hemodialysis solutions in adequate concentrations, efficiently transfers from the dialysate to the blood compartment, and binds to the transferrin in the plasma. This data combined with previous studies showing the safety of ferric pyrophosphate demonstrates the utility of the present invention as a means for providing bioavailable iron in a mammal, especially a dialysis patient requiring parenteral iron administration.

The invention has been described in an illustrative manner, and it is to be understood that the termninology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically describe.

Allegra V, Mengozzi G, Vasile A. Iron deficiency in maintenance hemodialysis patients: assessment of diagnosis criteria and of three different iron treatments. *Nephron* 1991;57: 175–182.

Byrd T F, Horwitz M A. Lactoferrin inhibits or promotes Legionella Pneumophilia intracellular multiplication in nonactivated and interferon gamma-activated human monocytes depending upon its degree of iron saturation. Iron-lactoferrin and nonphysiologic iron chelates reverse monocyte activation against Legionella Pneumophilia. *J Clin Invest* 1991;88(4):1103–1112.

Carver F G, Frieden E. Factors affecting the adenosine triphosphate induced release of iron from transferrin. *Biochemistry* 1978; 17(1):167–172.

Erslev A J. Erythropoietin. *N Engl J Med.* 1991;324(19): 1339–1344.

Eschbach J W, Cook J D, Scribner B H, Finch C A. Iron balance in hemodialysis patients. *Ann. Intern. Med.* 1977;87:710–713.

Hamstra R, Block M, Schocket A. Intravenous iron dextran in clinical medicine. *JAMA* 1980;243:1726–1731.

Harken A H, Simon M B, Hasilgrove J. Early ischemia after complete coronary litigation in the rabbit, dog, pig and monkey. *AM J Physiol* 1981;241:H202.

Health C W, Strauss M B, Castle W B. Quantitative aspects of iron deficency in hypochromic anemia. *J Clin Invest* 1932;11:1293.

Jacobs K, Shoemaker C, Rudersdorf R. Isolation and characterization of genomic and cDNA clones of human erythropoitin. *Nature* 1985;313:806–810.

Javaid N, Hasckle F, Pietsschnig B, et al. Interactions between infections, malnutrition and iron nutritional status in Pakistani infants. A longitudinal study. *Acta Paediatrica Scandinavica-Supplement* 1991;374:141–50.

Konopka K, Mareschal J C, Crichton R R. Iron transfer from transferrin to ferritin mediated by polyphosphate compounds. *Biochim. Biophys. Acta* 1981;677:417–423.

Konopka K, Mareschal J C, Crichton R R. Iron transferrin to ferritin mediated by pyrophosphate. *Biochem Biophys Res Commun* 1980;96(3):1408–1413.

Kumpf V, Hollanf E. Parenteral iron dextran therapy. *DICP Ann Pharmacother* 1990;24:162–166.

Levin N A. The impact of epoetin alfa: quality of life and hematocrit level. *Am J Kid Dis* 1992; XX(Suppl 1 (July)): 16–20.

MacDougall I, Hutton R, Cavill I, Coles G, Williams J. Poor response to the treatment of rental anaemia with erythropoietin corrected by iron given intravenously. *Br Med J* 1989;299:157–158.

Maurer A H, Knight L C, Siegel J A, Elfenbein I B, Adler L P. Paramagnetic pyrophosphate. Preliminary studies on magnetic resonance contrast enhancement of acute myocardial infarction. *Investigative Radiology* 1990;25(2): 153–63.

Morgan E H. Studies on the mechanism of iron release from transferrin. *Biochim. Biophys. Acta* 1979;580(2): 312–326.

Morgan E H. Iron exchange between transferrin molecules mediated by phosphate compounds and other cell metebolites. *Biochim Biophys Acta* 1977;499(1):169–177.

Nilsen T, Romslo I. Pyroposphate as ligand for delivery of iron to isolated rat-liver mitochondria. *Biochim. Biophys. Acta* 1984;766(1):2233–239.

Pascual J, Teruel J L, Liano F, Sureda A, Ortuno J. Intravenous Fegluconate-Na for the iron-deficent patients on hemodialysis. *Nephron* 1992;60:121.

Pollack S, Weaver J. Guinea pig and human red cell hemolystates release iron from transferrin. *J Lab. Clin Med.* 1985;105(5):629–634.

Pollack S, Vanderhoff G, Lasky F. Iron removal from transferrin. An experimental study. *Biochim. Biophys. Acta* 1977; 497(2):481–487.

Schaeffer R, Schaefer L. The Hypochromic red cell: A new parameter for monitoring or iron supplementation during r-huEPO therapy. *J Perinat Med* 1995;23:83–88.

Schaeffer R, Schaefer L. Management of iron substitution thearpy during r-HuEPO therapy in chronic renal failure patients. *Erythropoiesis* 1992;3:71–75.

Sillen L G, Martell A E. Stability contants of metal-ion complexes. The Chemical Society, London, 1964.

Van Wyck D B, Stivelman J, Ruiz J, Kirlin L, Katz M, Ogden D. Iron status in patients receiving erythropoietin for dialysis-associated anemia. *Kidney Int* 1989;35:712–716.

What is claimed is:

1. A composition comprising ferric pyrophosphate dissolved in a dialysis solution, wherein the dialysis solution is selected from the group consisting of peritoneal dialysis solution and hemodialysis solution.

2. A method of increasing the amount of bioavailable iron in a mammal by administering to the mammal during dialysis via a peritoneal dialysis solution or hemodialysis solution from 2 to 50 ug iron per deciliter of the peritoneal dialysis solution or hemodialysis solution, said iron in the form of ferric pyrophosphate dissolved in the peritoneal dialysis solution or hemodialysis solution, whereby the amount of bioavailable iron in the mammal is safely increased.

3. A method of iron administration to a dialysis patient through a dialysis solution selected from the group consisting of peritoneal dialysis solution and hemodialysis solution, said method comprising dialyzing the patient with said dialysis solution, wherein said dialysis solution contains from 2 to 50 ug of iron per deciliter of the dialysis solution, said iron in the form of ferric pyrophosphate soluble in the dialysis solution, whereby iron is safely administered to the patient via the dialysis solution.

4. A method of increasing the amount of bioavailable iron in a mammal by administering to the mammal during dialysis via a hemodialysis solution from 4 to 50 milligrams of iron per dialysis session, said iron in the form of ferric pyrophosphate dissolved in the hemodialysis solutions, whereby the amount of bioavailable iron in the mammal is safely increased.

* * * * *